US006803478B2

(12) United States Patent
Henning et al.

(10) Patent No.: US 6,803,478 B2
(45) Date of Patent: Oct. 12, 2004

(54) PROCESS FOR THE PREPARATION OF ALK(EN)YLPHOSPHORIC ESTER SALTS

(75) Inventors: Torsten Henning, Bad Soden (DE); Roman Morschhäuser, Mainz (DE); Matthias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/323,096

(22) Filed: Dec. 18, 2002

(65) Prior Publication Data

US 2003/0139622 A1 Jul. 24, 2003

(30) Foreign Application Priority Data

Dec. 20, 2001 (DE) .......................................... 101 63 316

(51) Int. Cl.⁷ ................................................. C07F 9/08
(52) U.S. Cl. ..................................................... 558/208
(58) Field of Search ......................................... 558/208

(56) References Cited

U.S. PATENT DOCUMENTS 4,118,443 A    10/1978   Klose ......................... 260/980

FOREIGN PATENT DOCUMENTS

DE     26 02 289     7/1977

OTHER PUBLICATIONS

English abstract for JP 61–093188, May 12, 1986.

XP–002236155, Chemical Abstract, vol. 120, No. 12, Mar. 21, 1994, abstract No. 137035, Koizumi, Yukimichi, et al., "Granular alkyl phosphate ester metal salts as antistatic agents for fibers and their manufacture", JP 05–186484, Jul. 27, 1993.

English abstract for JP 62–198690, Sep. 2, 1987.

*Primary Examiner*—Ceila Chang
*Assistant Examiner*—Ebenezer Sackey
(74) *Attorney, Agent, or Firm*—Richard P. Silverman

(57) ABSTRACT

The invention relates to a process for the preparation of alk(en)ylphosphoric ester salts which comprises reacting the alk(en)ylphosphoric esters in the form of their melts with a base. Advantageously, the alk(en)ylphosphoric esters do not need to be dissolved in a solvent prior to neutralization.

18 Claims, No Drawings

PROCESS FOR THE PREPARATION OF ALK(EN)YLPHOSPHORIC ESTER SALTS

The invention relates to a novel process for the preparation of alk(en)ylphosphoric ester salts.

Alk(en)ylphosphoric esters have excellent properties as detergents, and also a high emulsifying power and good ecotoxicological compatibility.

Of increasing importance is the use of solid, solvent-free phosphoric esters, in particular salts thereof, which, due to their neutral pH values, are very well tolerated by the skin and are advantageous as emulsifiers in cosmetic and pharmaceutical formulations.

The alkyl- and alkenylphosphoric esters are prepared in a known manner by reacting tetraphosphorus decaoxide and fatty alcohols to form mono- and diesters with small fractions of triesters. The phosphoric esters are dissolved in solvents for neutralization, and then reacted with bases, for example NaOH or KOH.

JP 62 198 690 describes the neutralization of phosphoric esters in a hydroxyl-containing, water-soluble reaction medium, for example propylene glycol.

For economical, ecological and performance reasons it would be desirable to find a solvent-free method for the preparation of alk(en)ylphosphoric ester salts.

Surprisingly, it has now been found that alk(en)ylphosphoric esters in the form of their melts can be neutralized with a concentrated aqueous or solid base to give alk(en)ylphosphoric ester salts.

Since the alk(en)ylphosphoric esters are not dissolved in a solvent, subsequent stripping off of same is unnecessary. Moreover, the residual water content in the alk(en)ylphosphoric ester salt can be minimized such that it is bonded as water of crystallization and does not have to be stripped off.

The invention provides a process for the preparation of alk(en)ylphosphoric ester salts of the formula (I) and/or of the formula (II)

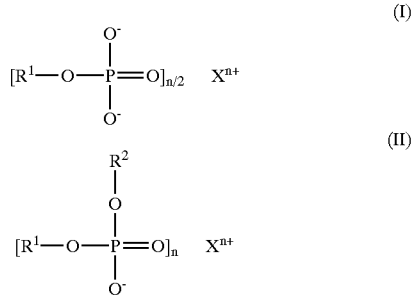

in which

R¹ and R² are identical or different and, independently of one another, are a linear or branched alkyl or alkenyl radical having 6 to 30 carbon atoms and $X^{n+}$ is a cation with the valency n, where n is an integer, which comprises reacting alk(en)ylphosphoric esters of the formula (III) and/or of the formula (IV)

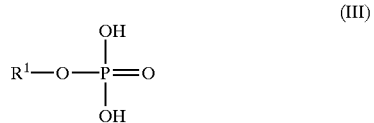

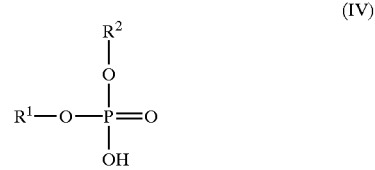

in the form of their melts with a base from which the cation $X^{n+}$ arises.

It may be expressly noted that the term base also includes mixtures of chemically different bases. In this case, the alk(en)ylphosphoric ester salts of the formulae (I) and (II) regularly contain different cations $X^{n+}$, which arise during the neutralization from the various bases.

The radicals R¹ and R² are preferably alkyl or alkenyl radicals having 8 to 22 carbon atoms.

The alk(en)ylphosphoric esters of the general formulae (III) and (IV) are generally prepared by condensation of phosphorus pentoxide or orthophosphoric acid with fatty alcohols.

Preferred fatty alcohols are caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, brassidyl alcohol and mixtures thereof.

The preparation of the alk(en)ylphosphoric esters often produces mixtures of mono-, di- and triphosphoric esters, the pH of which is usually in the range 2 to 5.

Of preference for the reaction are mixtures with a monophosphoric ester fraction greater than 60% by weight, preferably greater than 80% by weight. Fractions of triphosphoric esters do not interfere in the reaction.

The alk(en)ylphosphoric esters are preferably melted in a mixing-kneading reactor.

The bases may be organic or inorganic bases which are suitable for neutralizing the OH groups of the alk(en)ylphosphoric esters.

The base may be used as an aqueous solution, preferably as a concentrated aqueous solution, suspension or in the form of a powder. The concentration of the aqueous solutions/suspensions is preferably greater than or equal to 25% by weight, particularly preferably 50% by weight, especially preferably 75% by weight.

In a preferred embodiment, the total amount of water which originates from the base and/or the water of neutralization is such that it is bonded as water of crystallization in the solid phosphoric ester salt.

In a preferred embodiment, the base is used as a saturated aqueous solution. In the case of saturated aqueous solutions, a sufficiently good miscibility of the reactants with the simultaneous minimal introduction of water into the reaction mixture is ensured.

If the base is used in the form of a powder, this has the advantage that no water is introduced via the base, and the water formed during the crystallization is bonded as water of crystallization the solid phosphoric ester salt. Subsequent removal of residual water from the product can be dispensed with.

Preferred bases are metal hydroxides, metal oxides, ammonia, primary amines, secondary amines, tertiary amines, alkanolamines and/or amino acids. Preferred metal hydroxides are alkali metal hydroxides, preferably NaOH and KOH, alkaline earth metal hydroxides, preferably Ca(OH)$_2$, and alkaline earth metal hydroxides, preferably Al(OH)$_3$.

Preferred amines are primary amines with long-chain alkyl or aryl radicals having 6 to 30 carbon atoms, particularly preferably 16 to 22 carbon atoms.

Preferred alkanolamines are monoethanolamine, diethanolamine and triethanolamine.

Particularly preferred bases are alkali metal hydroxides, particularly preferably NaOH and KOH, very particularly preferably KOH.

Accordingly, the cations $X^{n+}$ in the formulae (I) and (II) are preferably metal ions, $NH_4^+$ and ammonium ions derived from amines, alkanolamines and amino acids. Preferably, n has the value 1, 2 or 3, particularly preferably 1 or 2, very particularly preferably 1.

The equivalent molar ratio of phosphoric ester(s) to base is preferably in the range 1:0.1 to 1:10, particularly preferably 1:0.5 to 1:2, especially preferably 1:0.9 to 1:1.1. Very particularly preferably, the ratio is 1:1.

The reaction of the alk(en)ylphosphoric ester with the base preferably takes place at temperatures of from 50 to 300° C., particularly preferably 100 to 180° C., over a period of from 0.1 to 10 hours, particularly preferably 0.1 to 5 hours, especially preferably 0.1 to 3 hours.

Advantageously, the reaction temperature is above the melting point of the end product, since sufficiently miscibility of the reactants is then ensured.

The alk(en)ylphosphoric esters are preferably initially introduced as melts and then reacted with the base.

The reaction is preferably carried out with mixing/kneading, preferably in a mixing-kneading reactor.

Surprisingly, it has been found that the quality and processability of the products increases if the reaction mixture is mixed/kneaded following the reaction at 50 to 300° C. for a further 0.1 to 6 hours at room temperature.

The mixing/kneading preferably takes place in a mixing-kneading reactor.

The products which are produced can be readily drawn off as a block product or flaked to give a flaked product or be drawn off in the form of pellets.

The alk(en)ylphosphoric ester salts prepared according to the invention are suitable for use in cosmetic and pharmaceutical formulations, in particular for the preparation of oil-in-water emulsions, but also of water-in-oil emulsions. They are preferably suitable for the preparation of alcohol-free emulsions.

The alk(en)ylphosphoric ester salts are usually used in amounts of from 0.1 to 10% by weight, preferably 0.3 to 4% by weight, based on finished formulations.

The emulsions can be used as skincare compositions, such as, for example day creams, night creams, care creams, nutrient cream, body lotions, ointments and the like. Further auxiliaries and additives which may be present are, inter alia, oily bodies, coemulsifiers, superfatting agents, fats, waxes, stabilizers, biogenic active ingredients, glycerol, preservatives, dyes and/or fragrances.

The examples below serve to illustrate the invention in more detail without, however, limiting it thereto. All percentages given are percentages by weight.

EXAMPLE 1

Preparation of the Potassium Salt of the Monocetyl Phosphoric Ester

1) Initial charge of 670 g of ®Hostaphat CC 100 (monocetyl phosphate, Clariant) in the mixing-kneading reactor (List) as melt at a temperature of 120° C.

2) Dissolution of 111.4 g of KOH pellets in 40 g of water at 80 to 90° C.

3) Slow addition of the KOH solution at about 80° C. into the operating kneader

4) Vigorous kneading at 150° C. for 15 minutes

5) Vigorous kneading at room temperature for a further 3 hours in an open mixing-kneading reactor, during which granulation takes place as a result of cooling 6) Formulation by grinding.

The product was a white to slightly yellowish powder with a melting point of from 120 to 130° C.

EXAMPLE 2

Preparation of the Potassium Salt of the Monocetyl Phosphoric Ester

1) Initial charge of 670 g of ®Hostaphat CC 100 (monocetyl phosphate, Clariant) in the mixing-kneading reactor (List) as melt at a temperature of from 160 to 180° C.

2) slow addition of 111.4 g of KOH powder 3) vigorous kneading at 160 to 180° C. for 3 hours 4) vigorous kneading at room temperature for a further 3 hours in an open mixing-kneading reactor, during which granulation takes place as a result of cooling 5) formulation by grinding.

The product was a white to slightly yellowish powder with a melting point of from 120 to 130° C.

What is claimed is:

1. A process for the preparation of alk(en)ylphosphoric ester salts of the formula (I) and/or of the formula (II)

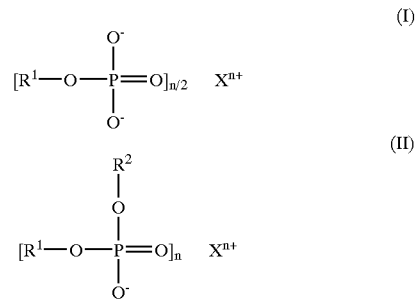

in which

R$^1$ and R$^2$ are identical or different and, independently of one another, are a linear or branched alkyl or alkenyl radical having 6 to 30 carbon atoms and $X^{n+}$ is a cation with the valency n, where n is an integer, which comprises reacting a mixture alk(en)ylphosphoric esters of the formula (III) and of the formula (IV)

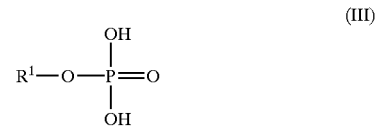

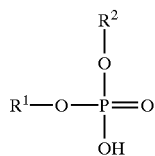

(IV)

in the form of their melts with a base from which the cation $X^{n+}$ arises, where the proportion of esters of the formula (III), based on the mixture, is greater than 60% by weight.

2. The process of claim 1, wherein the radicals $R^1$ and $R^2$ are alkyl or alkenyl radicals having 8 to 22 carbon atoms.

3. A process for the preparation of alk(en)ylphosphoric ester salts of the formula (I) and/or of the formula (II)

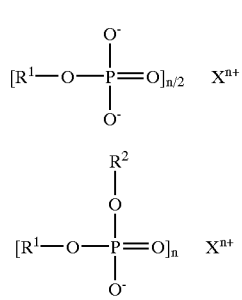

in which
R¹ and R² are identical or different and, independently of one another, are a linear or branched alkyl or alkenyl radical having 6 to 30 carbon atoms and
$X^{n+}$ is a cation with the valency n, where n is an integer, which comprises reacting a mixture at alk(en)ylphosphoric esters of the formula (III) and of the formula (IV)

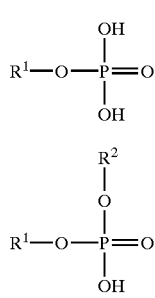

in the form of their melts with a base from which the cation $X^{n+}$ arises, wherein the base is a concentrated aqueous solution or a powder.

4. The process as claimed in claim 3, wherein the base is a saturated aqueous solution.

5. The process of claim 1, wherein the base is selected from the group consisting of metal hydroxides, metal oxides, ammonia, primary amines, secondary amines, tertiary amines, alkanolamines, amino acids, and mixtures thereof.

6. The process as claimed in claim 5, wherein the base is an alkali metal hydroxide and/or an alkaline earth metal hydroxide.

7. The process as claimed in claim 6, wherein the base is selected from the group consisting of NaOH, KOH, Ca(OH)$_2$, and mixtures thereof.

8. The process of claim 1, wherein an equivalent molar ratio of alk(en)ylphosphoric esters to the base is in the range 1:0.1 to 1:10.

9. The process of claim 1, wherein the reaction takes place in a reaction mixture at temperatures of from 50 to 300° C. over a period of from 0.1 to 10 hours.

10. The process as claimed in claim 9, further comprising mixing/kneading the reaction mixture following the reaction at 50 to 300° C. for a further 0.1 to 6 hours at room temperature.

11. The process of claim 1, wherein the alk(en)ylphosphoric esters are initially introduced as melts and are then reacted with the base.

12. The process of claim 1, wherein the reaction is carried out with mixing/kneading.

13. The process of claim 1, wherein the alk(en)ylphosphoric esters are a mixture comprising alk(en)ylphosphoric esters of the formulae (III) and (IV), where the proportion of alk(en)ylphosphoric esters of the formula (III), based on the mixture, is greater 80% by weight.

14. The process of claim 6 wherein the base is KOH.

15. The process of claim 8 wherein the equivalent molar ratio is 1:0.5 to 1:2.

16. The process of claim 8 wherein the equivalent molar ratio is 1:0.9 to 1:1.1.

17. The process of claim 1, wherein the reaction takes place in a reaction mixture at temperatures of from 100 to 180° C., over a period of from 0.1 to 5 hours.

18. The process of claim 1, wherein the reaction is carried out in a mixing-kneading reactor.

* * * * *